(12) United States Patent
Pearl et al.

(10) Patent No.: US 8,771,327 B2
(45) Date of Patent: Jul. 8, 2014

(54) APPARATUS AND METHOD FOR STIMULATING HAIR GROWTH

(75) Inventors: Henry Pearl, Naremburn (AU); David Michael Sinofsky, Delray Beach, FL (US)

(73) Assignee: Lexington LaserComb IPAG, St. Gallen (CH)

( * ) Notice: Subject to any disclaimer, the term of this patent is extended or adjusted under 35 U.S.C. 154(b) by 92 days.

(21) Appl. No.: 13/108,436

(22) Filed: May 16, 2011

(65) Prior Publication Data

US 2012/0123305 A1 May 17, 2012

Related U.S. Application Data

(63) Continuation-in-part of application No. 11/563,675, filed on Nov. 27, 2006, now abandoned, which is a continuation-in-part of application No. 10/295,487, filed on Nov. 15, 2002, now Pat. No. 7,201,764, which is a continuation-in-part of application No. 09/882,724, filed on Jun. 15, 2001, now Pat. No. 6,497,719.

(60) Provisional application No. 60/273,701, filed on Mar. 6, 2001.

(51) Int. Cl.
*A61N 5/06* (2006.01)
(52) U.S. Cl.
USPC .................. 607/90; 607/88; 607/96; 607/109; 128/898
(58) Field of Classification Search
USPC .............. 607/88–91, 96, 108, 109; 606/9, 10; 128/898
See application file for complete search history.

(56) References Cited

U.S. PATENT DOCUMENTS

| | | | |
|---|---|---|---|
| 1,948,990 A | 2/1934 | Mitlehner | |
| 2,397,757 A | 4/1946 | Schwedersky | |
| 6,053,180 A * | 4/2000 | Kwan | 132/232 |
| 6,363,215 B1 | 3/2002 | Cafaro | |
| 6,450,941 B1 * | 9/2002 | Larsen | 600/14 |
| 6,629,971 B2 * | 10/2003 | McDaniel | 606/9 |
| 6,663,659 B2 * | 12/2003 | McDaniel | 607/88 |
| 6,709,446 B2 | 3/2004 | Lundahl et al. | |

(Continued)

FOREIGN PATENT DOCUMENTS

| | | |
|---|---|---|
| EP | 1666016 A1 | 7/2006 |
| WO | 2005086846 A2 | 9/2005 |
| WO | 2007050144 A1 | 5/2007 |
| WO | 2007096344 A1 | 8/2007 |

OTHER PUBLICATIONS

Whelan, et al., Effect of NASA Light-Emitting Diode Irradatiation on Wound Healing, Journal of Clinical Laser Medicine & Surgery, vol. 19, No. 6, 2011, pp. 305-314, Mary Ann Liebert, Inc., USA.

*Primary Examiner* — Ahmed Farah
(74) *Attorney, Agent, or Firm* — Christopher & Wiesberg, P.A.

(57) ABSTRACT

A device for stimulating hair growth applied to a user's scalp. The device includes a housing. A plurality of light emitting diodes coupled to the housing operable to emit non-coherent light, the non-coherent light having at least two intensity peaks. A plurality of pairs of teeth extending from the housing, wherein the plurality of light emitting diodes are disposed between each pair of teeth; and wherein each of the plurality of pairs of teeth parts the user's hair to expose the scalp.

16 Claims, 18 Drawing Sheets

(56) References Cited

U.S. PATENT DOCUMENTS

| | | |
|---|---|---|
| 7,194,316 B2 | 3/2007 | Bousfield et al. |
| 2002/0077679 A1* | 6/2002 | Lo .................................. 607/90 |
| 2003/0093915 A1 | 5/2003 | Pearl et al. |
| 2004/0147984 A1 | 7/2004 | Altshuler et al. |

* cited by examiner

Fig. 4A
Fig. 4B
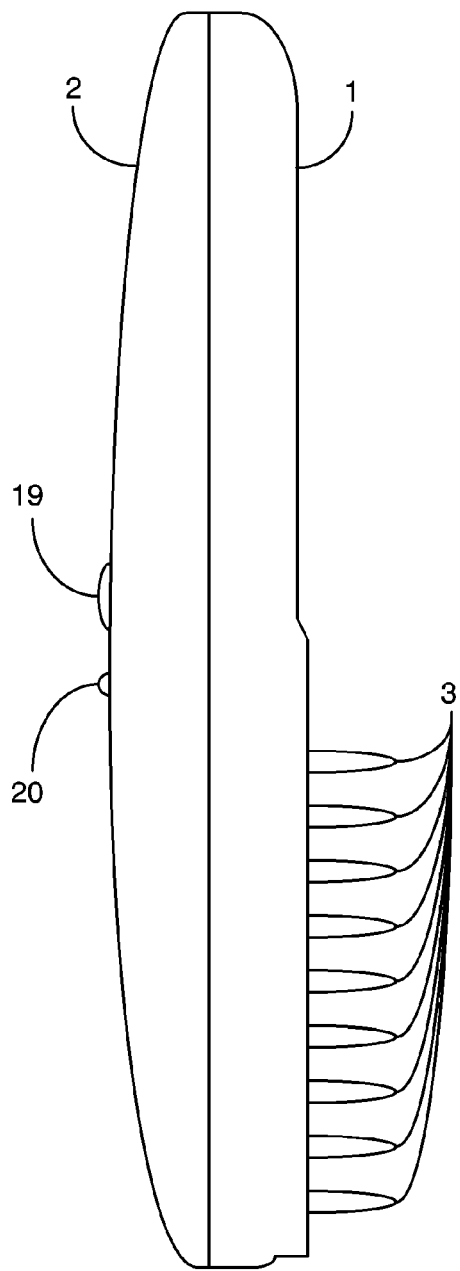
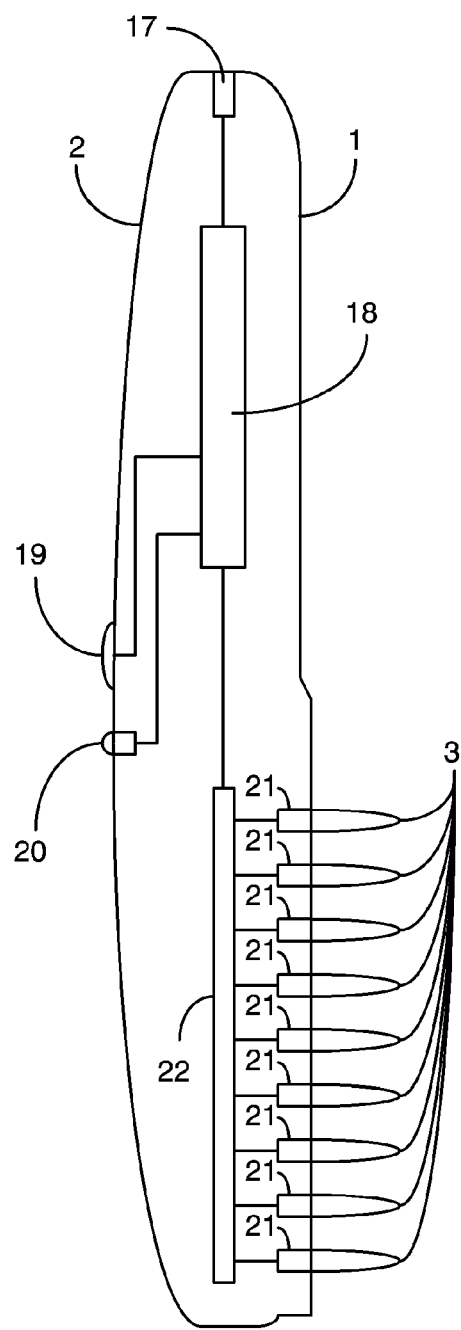

Fig. 9A
Fig. 9B
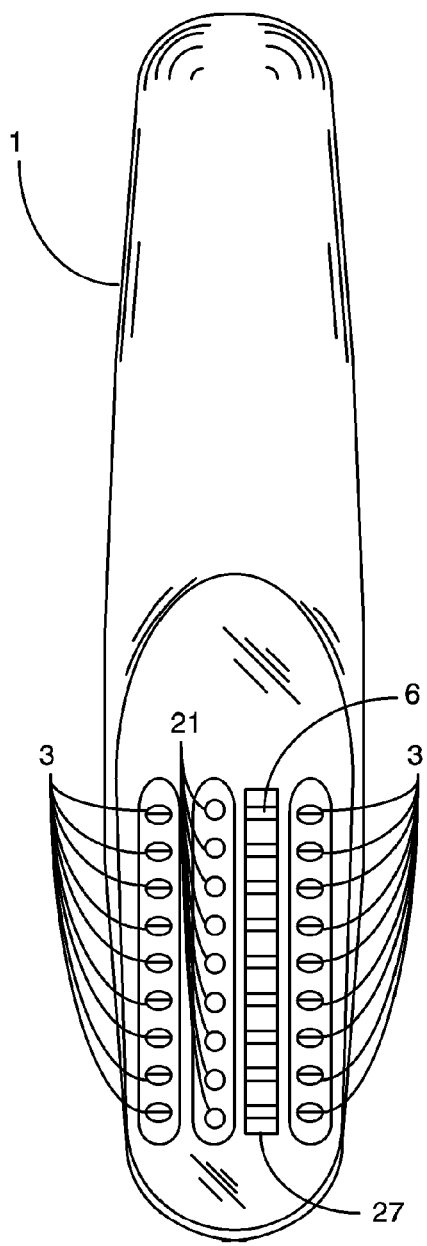
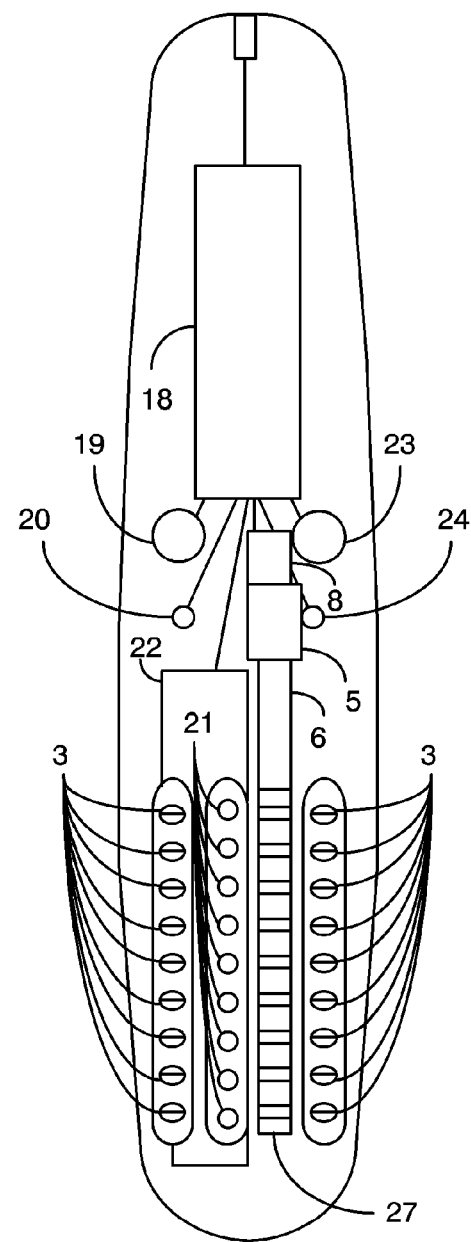

APPARATUS AND METHOD FOR STIMULATING HAIR GROWTH

CROSS-REFERENCE TO RELATED APPLICATION

This application is a continuation-in-part application of U.S. Ser. No. 11/563,675 entitled "Apparatus And Method For Stimulating Hair Growth," filed Nov. 27, 2006, the content of which is specifically incorporated by reference herein in its entirety, which is a continuation-in-part of U.S. Ser. No. 10/295,487 entitled "Apparatus and Method for Stimulating Hair Growth," filed Nov. 15, 2002, Issued on Apr. 10, 2007 as U.S. Pat. No. 7,201,764, the contents of which is specifically incorporated by reference herein in its entirety, which is a continuation-in-part of U.S. Ser. No. 09/882,724 entitled "Apparatus and Method for Stimulating Hair Growth," filed Jun. 15, 2001, Issued on Dec. 24, 2004 as U.S. Pat. No. 6,497,719, the contents of which is specifically incorporated by reference herein in its entirety, which was a non-provisional application of U.S. Ser. No. 60/273,701 entitled "Apparatus and Method for Stimulating Hair Growth," filed Mar. 6, 2001, now expired, the contents of which is specifically incorporated by reference herein in its entirety, and the related PCT application entitled "Improved Laser Comb Design/Function," bearing International Application No. PCT/AU00/00302 and filed Apr. 11, 2000 and naming Henry Pearl, one of the named inventors herein, as sole inventor, the contents of which is specifically incorporated by reference herein in its entirety.

STATEMENT REGARDING FEDERALLY SPONSORED RESEARCH OR DEVELOPMENT n/a

FIELD OF THE INVENTION

The present invention relates to a method and apparatus for treating alopecia, hair loss, and loss of hair color (i.e., graying). In particular, it relates to a method of treating the scalp or skin of an individual to increase the blood flow and general health of the skin to promote the healthier growth of hair and restoration of hair color.

BACKGROUND OF THE INVENTION

The loss of hair has traditionally been a problem for a substantial percentage of the population. Whether the problem is alopecia (male pattern baldness) or thinning hair, the individuals affected will generally find this to be distressing and detrimental to their appearance. In addition, the loss of hair will often make individuals appear to be older than they are. For this reason, a variety of attempts have been made to improve an individual's appearance by restoring the appearance of a full head of hair.

In addition, hair pieces have another drawback in that they may be inconvenient to use in situations, such as swimming, where they may become damaged or loosened. In this situation, the individual may be embarrassed due to the failure of the device. It would be desirable to improve the appearance of an individual's hair without having to resort to hair pieces fastened to an individual's head which are expensive and occasionally prone to failure due to environmental circumstances.

Those skilled in the art will recognize that more complicated mechanical solutions such as "hair weaving" exist. These more complicated solutions typically have the same drawbacks and problems as those associated with hair pieces. In addition, they are often more expensive than conventional hair pieces.

Another attempt to address this problem has been to surgically replace missing hair with "hair transplants." This surgical solution overcomes the problems created by the use of hair pieces in that the replacement hair transplants use the real hair of the individual, which results in a perfect color match and a natural appearance. In addition, the individual has no restrictions, such as those encountered in swimming and other activities, which were discussed above in regard to hair pieces. Unfortunately, this method of treating hair loss is expensive, and requires the use of medical professionals for the surgical hair transplant procedure. As a result, this procedure may not be available to a substantial portion of the public due to its high cost. It would be desirable to have a method of facilitating the growth of hair which was economically available to a substantial part of the entire public.

In addition to hair pieces and surgical transplants, pharmaceutical products have also been developed to encourage hair growth. These products can take the form of ingestible medications or topical skin treatments. Ingestible medications have been proven to encourage hair growth, but they have several significant drawbacks. In particular, they are typically prescription medications which require the cost and inconvenience of visiting a physician to obtain a prescription. In addition, the fact that they are prescription medications typically means that they will have a higher cost than non-prescription drugs. Perhaps more important than the issue of cost are the potential side effects of ingestible drugs. Quite often, the use of ingestible medications may result in serious health side effects, such as damage to the individual's liver, or other internal organs, or present other serious side effects. It would be desirable to have a method of stimulating hair growth which did not carry the risks of side effects inherent in ingestible pharmaceutical medications.

Another type of pharmaceutical medication has been the use of topical skin treatments. This type of medication is often similar to prescription medications with the same cost disadvantage of ingestible medications. While some are now available as over-the-counter preparations, they typically have a reduced strength and are less effective than are their prescription counterparts. In addition, they typically have to be applied every day to achieve and maintain their desired results. It would be desirable to have an effective low-cost method of stimulating hair growth which did not require potential visits to a physician, a continuous use of expensive medications, and daily treatments to ensure results.

Scientists in Europe and Asia have found over the last 25 years that lasers can be used to stimulate hair growth. Devices have been developed having structures similar to a large floor mounted, or chair mounted, helmet. These devices contain multiple laser assemblies, and are designed to irradiate the individual's entire scalp and hair with laser energy. It is been found that there are several disadvantages associated with this approach. In particular, these are typically very large and expensive commercial devices which are found in beauty salons and spas. In order to take advantage of them, an individual will go to the establishment where the devices are located and pay for treatments on a per treatment basis. Over time, this represents a fairly expensive proposition for the individual, and typically requires a trained operator to conduct the treatment.

The helmet-like structure of this device creates an additional disadvantage. Since the device covers the head of the individual, a substantial portion of the laser energy which is intended for application to the individual's scalp is blocked by the hair of the individual, thinning though it may be, which effectively forms a canopy over the individual's scalp. It would be desirable to have an inexpensive method of applying light treatment phototherapy, which does not require an individual to go to a specific location where large laser devices are used, which does not require the individual to pay every time a laser treatment is taken, and which maximizes the amount of laser energy applied to the scalp while minimizing the amount of laser energy which is blocked by the individual's hair Likewise, it would be desirable to have a laser treatment device which has a relatively small number of diodes, and which could apply light energy to the individual's scalp without interference by the individual's hair.

Another problem associated with hair is the loss of hair color (i.e., graying) which has the effect of making individuals appear to be older. Individuals often attempt to treat this problem by dying their hair. Unfortunately, this method of treatment has several disadvantages. For example, as was the case with hair pieces, discussed above, it can be difficult to produce the proper hair color such that it is not obvious that the hair was dyed. In addition, dyed hair tends to fade over time which results in re-appearance of the grey hair and a persistent change in color. Individuals who dye their hair typically have to re-dye their hair periodically, Of course, this represents an ongoing expense and inconvenience to the individual. Further, unless the dying process is performed by a trained individual, the results may be undesirable and unattractive. This further increases the cost of hair dying due to the need to hire a trained professional to perform the process. It would be desirable to have a method of treating loss of hair color without having to have an ongoing expense for dyes, or an ongoing expense for trained professionals to apply the dyes, and an ongoing inconvenience.

It has also been found that non-coherent light, while lacking the characteristics of power concentration inherent in laser light, can provide stimulation to the scalp which has beneficial and therapeutic effects in terms of stimulating the natural growth of hair.

While providing several methods of treating alopecia, hair loss, and graying, the prior art has failed to provide an apparatus which is inexpensive to manufacture, has a minimum number of components, minimizes the amount of laser energy blocked by an individual's hair, and can be used without leaving the individual's home or using costly commercial equipment and trained personnel.

SUMMARY OF THE INVENTION

The present invention provides for a device for stimulating hair growth applied to a user's scalp. The device includes a housing; a plurality of light emitting diodes coupled to the housing operable to emit non-coherent light, the non-coherent light having at least two intensity peaks; a plurality of pairs of teeth extending from the housing, wherein the plurality of light emitting diodes are disposed between each pair of teeth; and wherein each of the plurality of pairs of teeth parts the user's hair to expose the scalp.

The present invention also provides for a method of stimulating hair growth on a user's scalp. The method includes exposing the scalp using a hand-held device and emitting non-coherent light onto the scalp from the hand-held device.

The present invention provides for a device for stimulating hair growth applied to a user's scalp. The device includes a housing; a plurality of light emitting diodes coupled the housing emitting at light including a first intensity peak having a wavelength between approximately 425 nm and 500 nm, and a second intensity peak having a wavelength between approximately 900 nm and 1200 nm; a plurality of pairs of teeth extending from the housing, wherein the plurality of white light emitting diodes are disposed between each pair of teeth, wherein each of the plurality of pairs of teeth parts the user's hair to expose the scalp; and a photoactive cream disposed within the housing, the photoactive cream being dispersable to the scalp.

BRIEF DESCRIPTION OF THE DRAWINGS

FIG. 4A is a side external view of an alternative embodiment which uses a non-coherent light source to provide light energy to a user's scalp;

FIG. 4B is a cutaway side view of the alternative embodiment of FIG. 4A. This figure illustrates the major components used by this embodiment;

FIG. 9A is an external bottom view of the alternative embodiment of FIG. 7. This figure illustrates the alignment of multiple light sources between associated sets of teeth;

FIG. 9B is a cutaway bottom view of the alternative embodiment of FIG. 8A. This figure illustrates the location of the major components used by this embodiment;

DETAILED DESCRIPTION OF THE INVENTION

Figure 1:
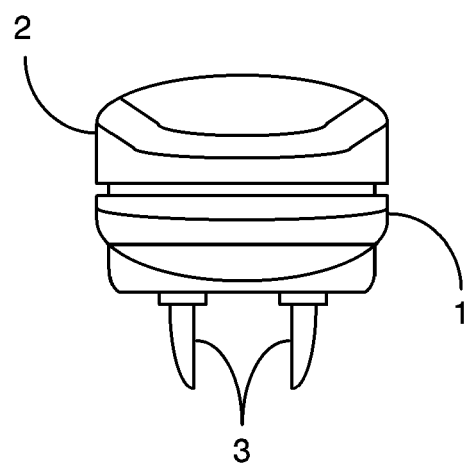
FIG. 1 is an end view of a embodiment of the device which shows opposing furrow forming teeth extending outward from either side of the device.

Prior to a detailed discussion of the figures, a general overview of the system will be presented. For ease of discussion, the term "scalp" will be used to describe the conventional definition which describes the hair covered portion of skin on the user's head, and in addition, any skin surface where hair is desired to be grown (e.g., a beard, etc). Likewise, the term "teeth" is used to refer to any projections which extend from the body of the device toward the user's scalp, and which are designed to part the user's hair in front of a trailing light beam. The shape of the teeth is not important as long as they accomplish the goal of parting the user's hair.

In an exemplary embodiment, the teeth are also intended to be non-light carrying teeth, which travel in front of, or behind, an associated light beam which may be laser light, non-coherent light, or a combination thereof. In particular, this embodiment envisions non-light carrying teeth which are substantially parallel to, and offset from, associated light beams projected from the device. The device is intended to be moved over the user's scalp such that as the teeth move through the user's hair, they create a part therein. The associated light beam which trails after the teeth is able to reach the surface of the user's scalp because of the part created by the teeth.

It is been found that the application of light can stimulate natural processes within the body, and particularly, within the scalp such that a variety of therapeutic results can be achieved. There has been, for example, a substantial amount of research done on the use of phototherapy energy to stimulate the body's natural processes to heal wounds, apply skin therapy, etc. The advantage of using the coherent light of a laser is that coherent light tends to concentrate power such that a greater effect can result from the application of a particular energy level. However, non-coherent light will also produce therapeutic and healing results when applied to the skin. It only differs from coherent light in the sense that its energy is not concentrated in the form of laser beam. The device described herein has several embodiments including a laser embodiment which emits only coherent light, a non-laser embodiment which emits only non-coherent light, and a mixed embodiment which emits both coherent and non-coherent light. The general discussion of the laser, the non laser, and the next embodiments will now be presented.

It has been found that low-power lasers may be used in a variety of therapeutic applications. For example, low-power lasers are used widely for a variety of cosmetic applications such as skin care, scar reduction, wound healing and the like. In addition, it has also been found that the application of low-power laser light to an individual's scalp will assist the hair's natural ongoing replacement process and improve the scalp's condition.

One of several factors associated with the use of lasers to stimulate hair growth is that laser treatments tend to increase scalp blood circulation. In fact, studies have shown that the application of laser energy to the scalp of a user can increase scalp blood circulation by more than fifty percent without significant changes in scalp temperature. This results in the skin receiving a more abundant supply of nutrients, and in turn, the structures in the skin, such as hair follicles, also receive a more abundant supply of nutrients and necessary materials from the body.

Microscopic studies have shown laser energy increases circulation and oxygenation of the blood to the scalp and hair bulb; removes calcification and blockages around the hair bulb; as well as increases cell replacement or regenerative activity. These factors help hair to improve in fullness, shine, body and elasticity. Problems such as over-oily or dry scalp, dandruff and itchiness can also be reduced. Research on the use of low level lasers indicates that application of a low level laser to an individual's scalp will normalize metabolism of tissues, improve trophism (blood cell nutrition), and assure a regular sebaceous secretion. Measurements taken from scalps treated by low level laser indicate that hair bulbs are strengthened, hair growth can be measurably ascertained, and hair color will darken.

The increase in blood flow helps as follows: in the human scalp, the follicle in which the hair grows is attached to the scalp by a structure known as the Papilla. The Papilla provides a path for nutrients in the blood to reach the cells in the hair. The laser treatment described herein improves both the condition of the Papilla itself, as well as the blood flow reaching the Papilla. The unique structure of the handheld device presented herein provides an unobstructed path for laser light, and/or non-coherent light, to the Papilla which results in the scalp being bathed in light energy.

Another factor associated with the use of lasers is "energization." Energization can be explained as follows: Light is energy. The use of a laser light on scalp and hair follicles provides high levels of light which are used by the cells in the scalp and hair to assist in the normal chemical processes performed by those cells. The scientifically agreed-upon term for this is photobiostimulation. The most common example of light converting into chemical energy is photosynthesis, where plants are fed via light converted into chemical energy. In a similar way, laser light penetrates into soft tissue and increases the action of adenosine triphosphate (ATP), a molecule that is a major carrier of energy from one reaction site to another in all living cells. By doing so, laser light increases the energy available to cells so they take in nutrients faster and get rid of waste products. Because of this benefit, scientists and physicians have been using low level laser over the past 30 years to accelerate wound healing and regenerate tissue.

Yet another factor associated with the use of laser light is known as "vibration." Soft tissue and fluids in our bodies actually vibrate. The vibration occurs within a frequency range similar to that of low powered, red-light laser. In fact, one scientific theory holds that cells are largely dependent for healthy function on an exchange of energy and information with surrounding cells. This is achieved via individual wave systems by which cells communicate through inter-connective plasma by vibration. A cell is in an unhealthy state when its vibrations become irregular or out-of-step with this common communications system. However, it can be brought back into vibratory "harmony" being irradiated with low level laser working at quantum level.

While the benefits of low-power laser treatments are known, attempts to take advantage of laser technology for the purpose of stimulating hair growth has produced limited results. In particular, when there is existing hair growth on the scalp being treated (i.e. as would be the case for individuals with thinning hair who are balding or experiencing alopecia) conventional laser beam devices do not satisfactorily penetrate the hair. As a result of the pre-existing hair blocking the path of the laser beam when it is aimed at the scalp, the effectiveness of the laser treatment is substantially reduced.

Another problem related to prior art laser treatment devices is that they tend to be large devices which are heavy and immobile. As a result, they would usually be found in a salon or clinic where the user would be charged each time the user obtained a treatment. Further, since these devices typically have fixed locations, they would not be available to the user when traveling, and they would be inconvenient to access even when the user was not traveling.

Prior art attempts to provide handheld devices have resulted in many undesirable drawbacks. For example, these devices tend to be large, bulky and complex due to the use of multiple laser modules and/or fiber optics which each produce a laser beam directed at a user's scalp. These devices also are difficult to manufacture due to the need to align the multiple lasers, or, in the case where fiber optics are used, to convey the laser energy into each fiber-optic by way of a complex lens system.

The invention provided herein solves all of the foregoing problems. The invention is a handheld, comb-like device which emits a row of phototherapy treatment beams, which may be produced by multiple independent phototherapy treatment beams. Each phototherapy treatment beam in the row of phototherapy treatment beams has a pair of associated teeth which are positioned in regard to the phototherapy treatment beam such that as the handheld device is pulled though the individual's hair, one tooth parts the hair in front of the phototherapy treatment beam and the second tooth follows the phototherapy treatment beams holding the hair apart. By moving the hair in this manner, the two rows of teeth function to form furrows in the hair, thereby exposing the user's scalp to the phototherapy treatment beam. This eliminates interference with the laser beam by the user's hair and delivers more phototherapy treatment beams directly to the user's scalp.

The invention overcomes the problem caused by pre-existing hair interfering with the laser beams by placing the phototherapy treatment beam between two rows of teeth which create "parts" (i.e., furrows) in the user's hair which are aligned with associated phototherapy treatment beams generated by the device. As a result of this aligned parting of the user's hair, the pre-existing hair is moved out of the way of the phototherapy treatment beam and the user's scalp receives the full benefit of the phototherapy treatment.

In one exemplary embodiment of this invention, the means by which the phototherapy treatment beams reaches the scalp is by way of a row of phototherapy treatment beams being preceded by a row of teeth that part the hair to expose the skin in advance of the row of phototherapy treatment beams, for example, laser beams. The row of teeth are aligned with the laser beams such that each tooth proceeds in advance of its respective beam to part the hair in front of the beam (i.e., forming a furrow) thereby ensuring that the beam is directed to the scalp and not blocked by the user's hair. In addition, the phototherapy treatment beams are followed by a second row of teeth which are also aligned with the row of phototherapy treatment beams. This second row of teeth allows the comb to be used in either direction for the convenience of the user. The second row of teeth also provides the benefit of keeping the hair parted for a slightly longer period of time to ensure that the hair does not fall back in place too quickly after the first row of teeth passes through the hair.

It has also been found that stimulation of the skin using non-coherent light also produces beneficial results. In particular, non-coherent light will stimulate the skin such that the ability of the skin to nourish and produce thick healthy hair is enhanced in the same manner as was done by the laser. However, the same problem encountered with delivery of laser energy to a patient's skin, namely, interference of the light beam by the patient's hair, also occurs when attempting to deliver non-coherent light energy to the skin surface. As was the case above, the comb structure used by the laser based embodiment will effectively allow access to substantial areas of the scalp by the non-coherent light.

It is also been found that a laser can be combined with a source of non-coherent light source. This provides an advantage in that while the laser uses a narrow frequency bandwidth, the non-coherent light source will deliver additional energy over a wider bandwidth. This maximizes the stimulation of the skin tissue and enhances its ability to support and nourish the growth of thick and healthy hair. In one embodiment, both laser energy and non-coherent light energy can be selectively and independently activated to provide a user with the ability to use either or both energy sources. Regardless of the type light energy provided, light beam are intended to be associated with particular teeth, and trail the teeth such that the light reaches the skin at the bottom of the furrow created by the teeth. A more detailed discussion of the figures now follows.

FIG. 1 shows an end view of an exemplary embodiment of the invention that illustrates the arrangement of components in the device. The components of the device are held together and supported by a lower housing 1 and an upper housing 2. Two rows of teeth 3 extend down from a lower housing 1. During use, the teeth 3 are combed though the user's hair in the same manner as an ordinary comb would be used.

The device may include two parallel rows of teeth 3 projecting downward from a bottom housing 1. One or more laser beams project outward from the device between the two rows of teeth 3. Further, they are aligned with the teeth 3 such that the laser beam is projected into the furrow when the handheld device is moved in either direction across the user's scalp.

This unit is designed to be a self-contained, handheld, device which applies a low-level phototherapy treatment, for example, a laser beam, directly to the scalp of a user without having the hair of the user interfere with the phototherapy treatment. In use, the user brushes the teeth 3 through the user's hair in the same manner as the user would use a hair brush. A laser beam 8 is aligned with each of the teeth 3 in the device such that the laser beam follows the "furrow" created by the teeth 3 as they move though the user's hair. By parting the hair in front of the laser beam in this manner, the laser beam is able to reach the bottom of the furrow (i.e., the scalp) without interference from the hair. This is a substantial improvement over prior art techniques which used helmet-like structures to direct laser energy directly to the user's head without taking into consideration the fact that most of the laser beam energy would be prevented from reaching the user's scalp by the user's hair.

In addition to being more effective than prior art devices in terms of the actual application of laser energy to the scalp, the embodiments disclosed herein are also superior to prior art devices in that they are extremely lightweight and portable. They can be manufactured such that they can be plugged into a wall socket for electrical energy, or alternatively, it can be battery operated to further add to the user's convenience. In addition, the reflector 6 allows a single laser to be used rather than the multiple lasers used by prior art devices.

Figure 2:
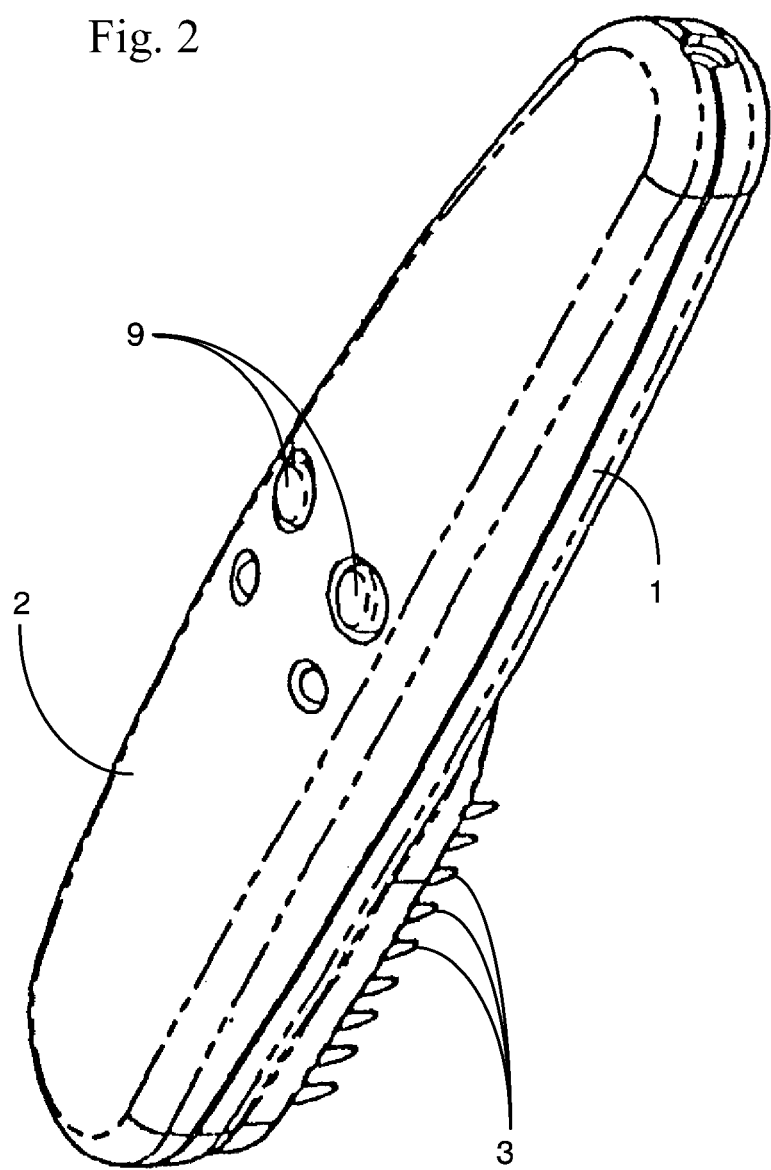
FIG. 2 is a top perspective view of an embodiment of the device which illustrates the control switches on the top of the device and the furrow forming teeth extending from the bottom of the device.

FIG. 2 is a perspective view of an exemplary embodiment of the handheld device. In this view, the teeth 3 are shown projecting downward from lower housing 1, and control switches 9 are shown located on the upper housing 2.

Figure 3:
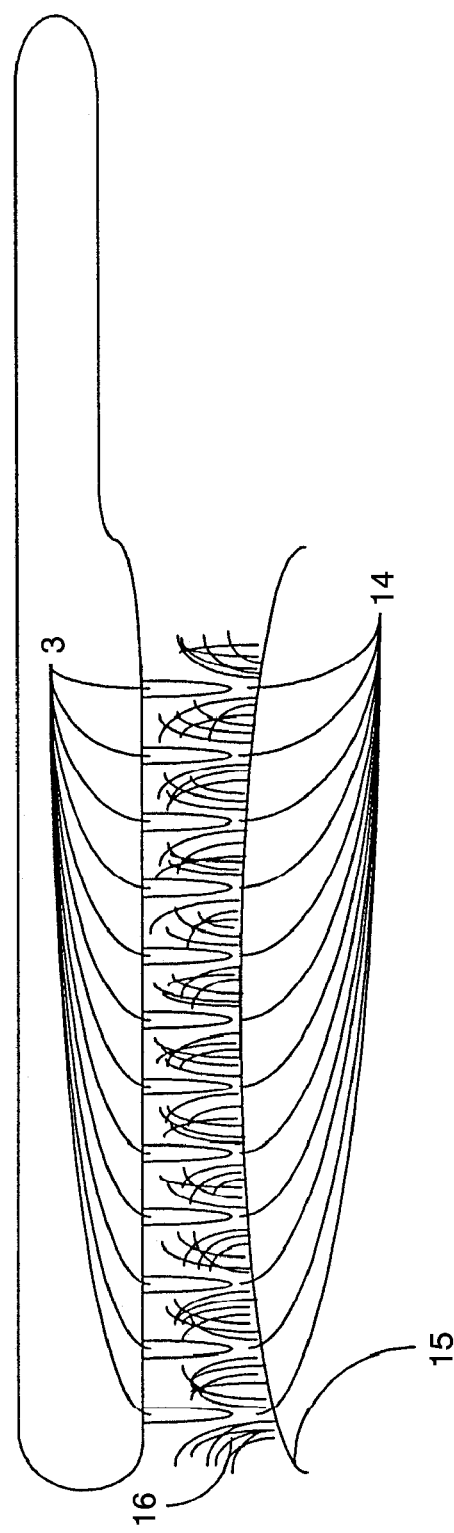
FIG. 3 is an illustration of a embodiment of the device in which an individual's hair is being furrowed to maximize the amount of laser energy applied to the individual's scalp.

FIG. 3 illustrates how the teeth 3 were used to produce furrows 14 in the individual's hair 16. This figure has a side view illustrating the teeth 3 being pulled through the individual's hair 16 while in close proximity to the individual's scalp 15. As can be seen, the movement of the teeth 3 though the hair 16 pushes the hair 16 aside to form furrows 14. As the hair forms furrows 14, the scalp 15 between the teeth 3 is exposed. Since the laser beam is aligned between the two opposing teeth for each furrow 14, the laser beam is directed to the surface of the scalp 15 which has been exposed by the furrow 14. The advantage provided by furrowing the hair 16 is that a high percentage of the laser energy is effectively applied to the scalp 15, and the hair 16 is prevented from interfering with the application of laser energy to the scalp 15.

FIG. 4A illustrates an external side view of an alternative embodiment in which the laser 8 is replaced with a non-coherent light source. In this embodiment, upper housing 2 and lower housing 1 support the set of teeth 3 in the same manner as was done in the foregoing embodiments. In addition, an activation switch 19 and a status indicator 20 are also shown.

FIG. 4B is a cutaway side view of the alternative embodiment illustrated in FIG. 4A. In this figure, a power attachment plug 17 is illustrated. Plug 17 attaches to a conventional power cord (not shown). Plug 17 is attached to a power source 18 which is designed to distribute power to the various components under control off the power activation switch 19. When the device is activated, status indicator 20 is illuminated for the user's convenience.

Those skilled in the art will recognize that power supplies are well-known in the art, and that other changes can be made to power source 18. For example, power source 18 can be powered by batteries, by an input power source, via plugs 17, or by a combination of both.

Once the device has been activated, power will be supplied from the power source 18 to emitter control circuit 22. Emitters 21 are controlled by emitter control circuit 22 which regulates the amount of time that emitters 21 are active. As can be seen from this figure, emitters 21 are aligned with teeth 3. The light emitters 21 can be implemented by any suitable technology. However, in this embodiment the emitters 21 are shown as LEDs for ease of discussion.

Figure 5A:
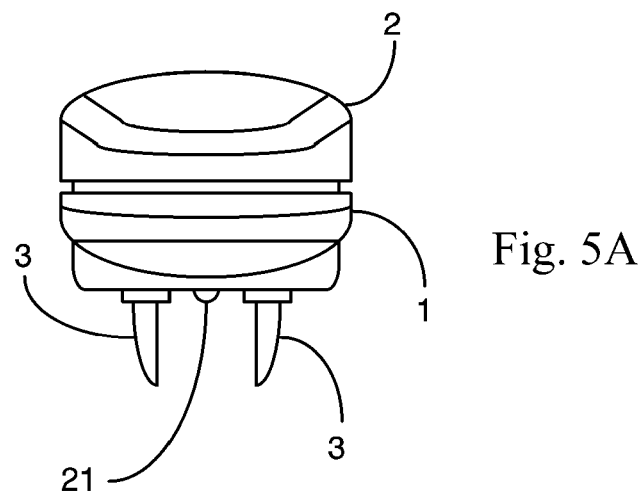
FIG. 5A is an external end view of the alternative embodiment of FIG. 4A which illustrates the placement of the non-coherent light source between two rows of teeth.

In FIG. 5A, an external end view of an exemplary embodiment of FIG. 4A is illustrated. Upper housing 2, lower housing 1, and teeth 3 are similar to those shown in the previous embodiments. In addition, the emitters 21 are also shown positioned between the teeth 3.

Figure 5B:
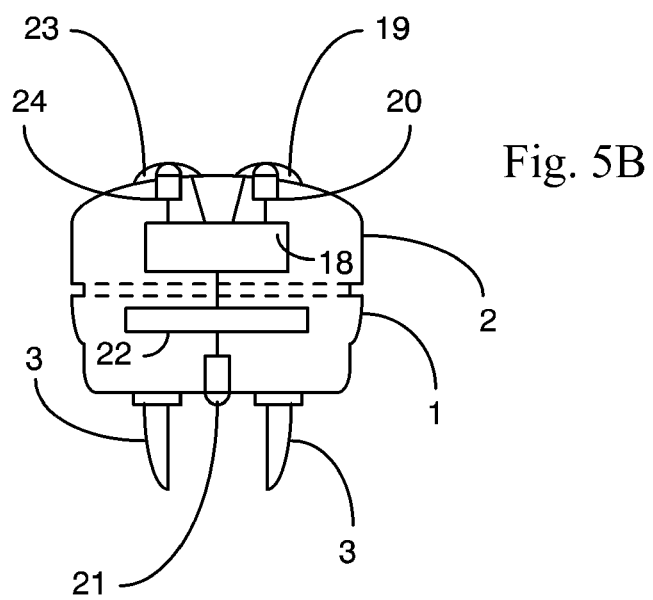
FIG. 5B is a cutaway end view of the alternative embodiment of FIG. 4A.

FIG. 5B is a cutaway end view of the embodiment of FIG. 5A. When power activation switch 19 is activated, it activates power source 18. Once power source 18 is activated, it activates status indicator 20 which illuminates to indicate that power has been turned on. Also shown in this figure is emitter activation switch 23, which when turned on gates power to emitter control circuit 22 which then activates emitters 21.

Figure 6A:
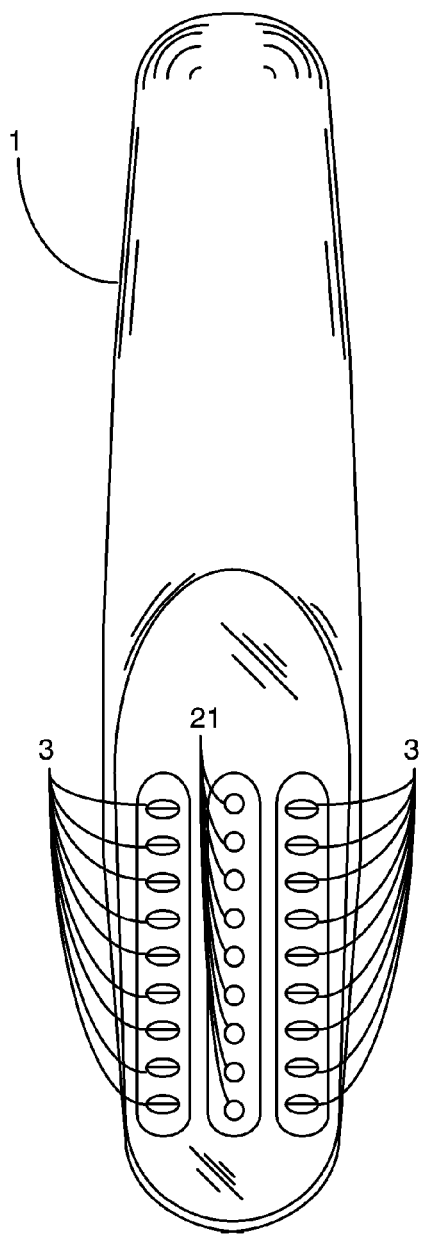
FIG. 6A is an external bottom view of the alternative embodiment of FIG. 4A. This figure illustrates the alignment of multiple light sources between associated sets of teeth.
Figure 6B:
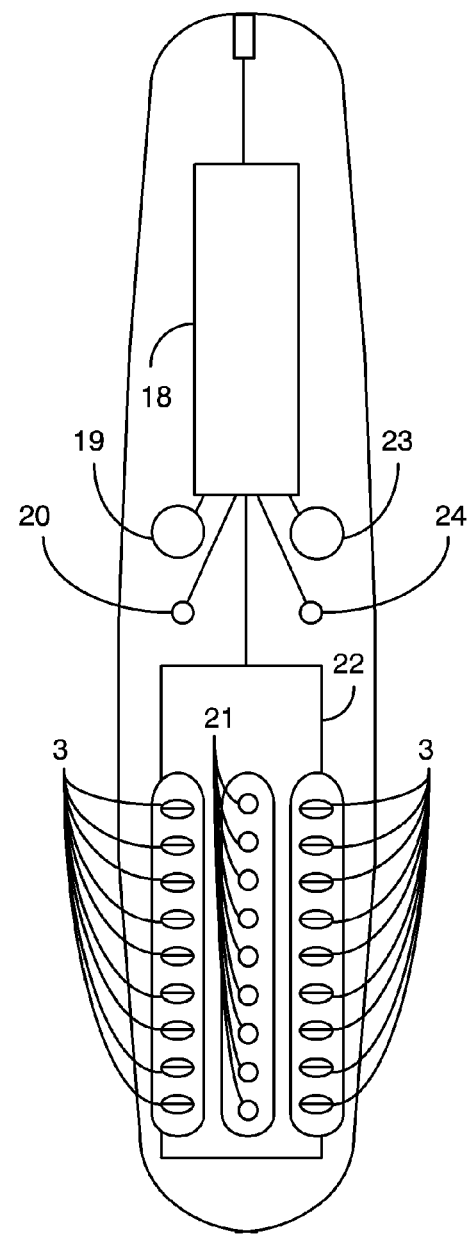
FIG. 6B is a cutaway bottom view of the alternative embodiment of FIG. 4A. This figure illustrates the location of the major components used by this embodiment.

FIG. 6A is a bottom external view of the embodiment of FIG. 4A. This view better illustrates how the emitters 21 are each aligned between associated pairs of teeth 3. Likewise, FIG. 6B illustrates a cutaway bottom view of the embodiment of FIG. 4A. This view also illustrates the basic components of the system which are power source 18, the emitter control circuit 22, the emitters 21, the teeth 3, and the control switches 19, 23 and indicators 20, 24.

Figure 7:
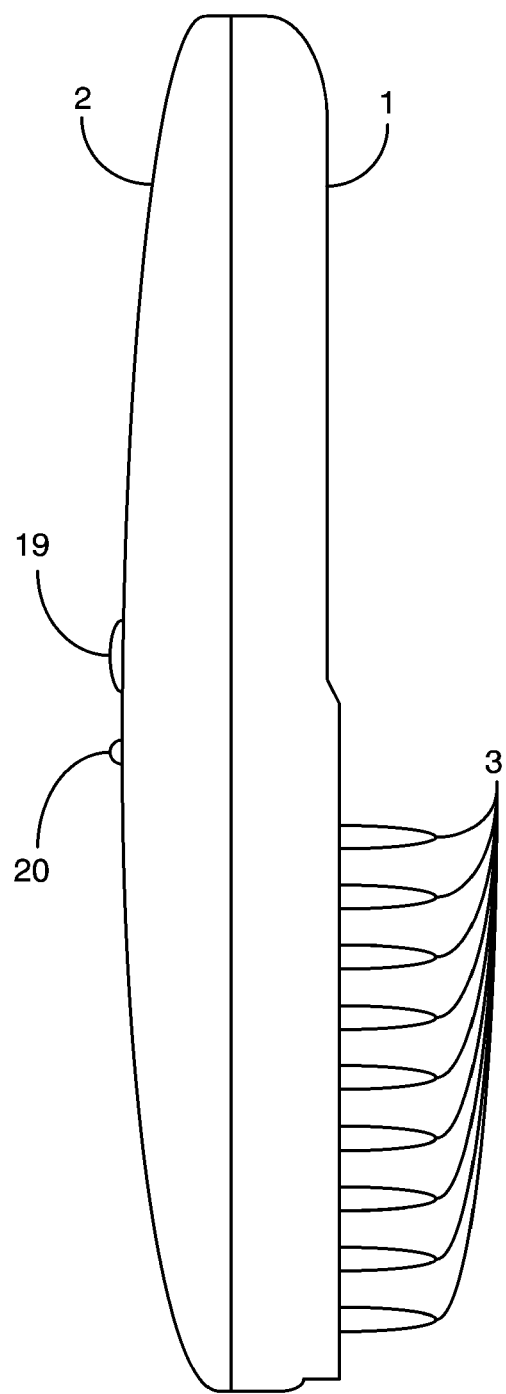
FIG. 7 is an external side view of another alternative embodiment which provides both coherent and non-coherent light.

In FIG. 7, a side external view of an alternative embodiment is illustrated. In this embodiment, the laser 8 which provided coherent light in previous embodiments is combined with emitters 21 which produce non-coherent light. As a result, energy can be concentrated in a small bandwidth by the laser 8, while broad bandwidth energy is simultaneously provided by the emitters 21.

Figure 8A:
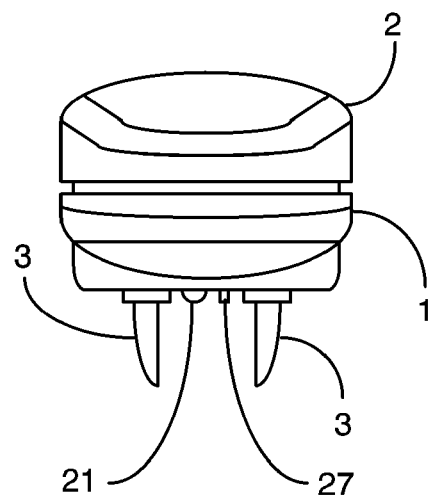
FIG. 8A is an external end view of the alternative embodiment of FIG. 7 which illustrates the placement of the coherent and non-coherent light sources between two rows of teeth.

FIG. 8A is an external end view of the embodiment of FIG. 7A. This figure illustrates the upper housing 2, lower housing 1, and the teeth 3 shown in previous embodiments. In addition, it also illustrates the adjacent locations of the emitters 21 and the laser window 27.

Figure 8B:
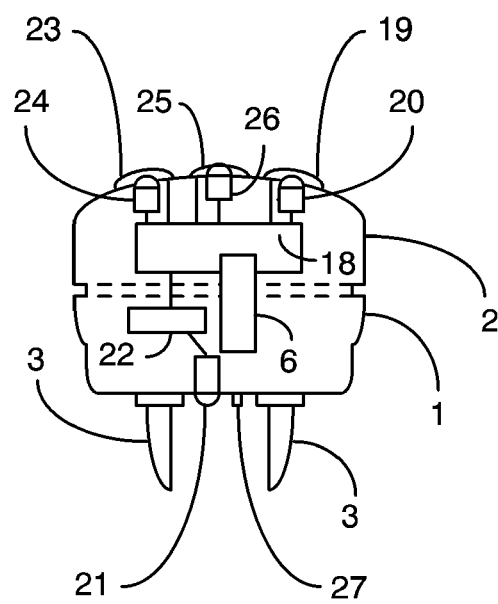
FIG. 8B is a cutaway end view of the alternative embodiment of FIG. 7.

FIG. 8B is an end cutaway view of the embodiment of FIG. 8A. This figure illustrates the side-by-side positioning of the emitters 21, and the laser reflector 5. In addition, this figure also illustrates a separate laser activation switch 25 and a laser status indicator 26.

In FIG. 9A, an external bottom view of the embodiment of FIG. 7A is shown. This embodiment better illustrates the relative location of the emitters 21 in relation to the laser windows 27. Likewise, FIG. 9B is a bottom cutaway view of the embodiment of FIG. 9A. This figure also illustrates the side-by-side positioning of the components associated with the emitters 21, and the laser 8.

An advantage of this embodiment is that the patient can use the broadband power provided by the emitters 21 alone, the patient can use the narrow band concentrated laser power provided by the laser 8, or the patient can use both simultaneously.

Figure 10:
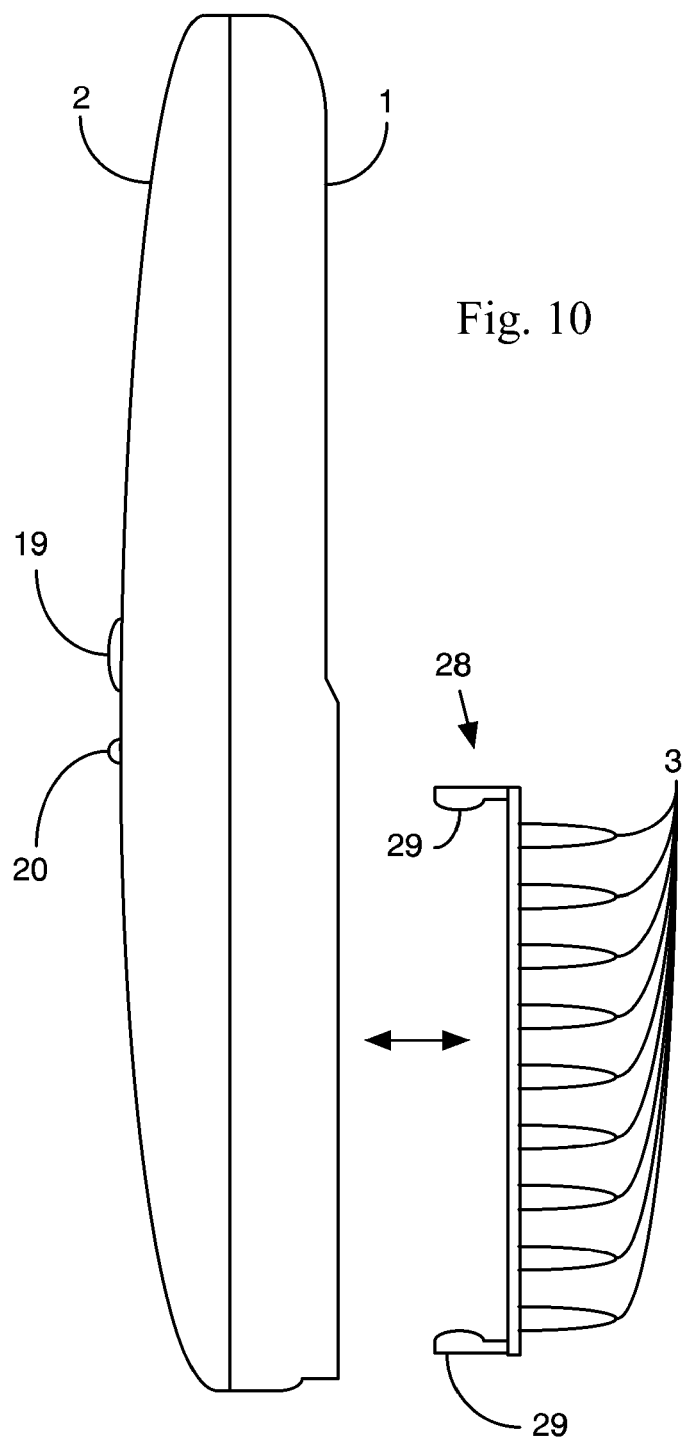
FIG. 10 is a side view of an alternative embodiment which uses a detachable teeth assembly.

FIG. 10 is a side view of an alternative embodiment which uses a detachable teeth assembly 28. In this embodiment, detachable teeth assembly 28 is secured to the lower housing 1 by snap-on connectors 29. Those skilled in the art will recognize that detention teaches the 28 can be connected via any convenient means, such as snap-on connectors, sliding attachments, adhesives, screws, etc. The only requirement is that the attachment means securely connect the teeth assembly 28 to the lower housing 1.

An advantage provided by the detachable teeth assembly 28 is that it allows convenient replacement of teeth should they become damaged. Further, the detachable teeth assembly 28 allows multiple individuals to use the same device.

Figure 11:
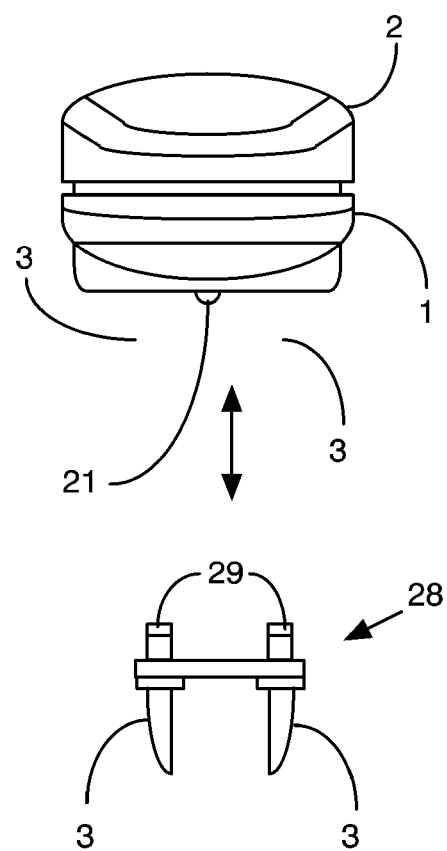
FIG. 11 is an end view of an alternative embodiment which uses a detachable teeth assembly.

FIG. 11 is an end view of an alternative embodiment which uses a detachable teeth assembly 28.

Figure 12:
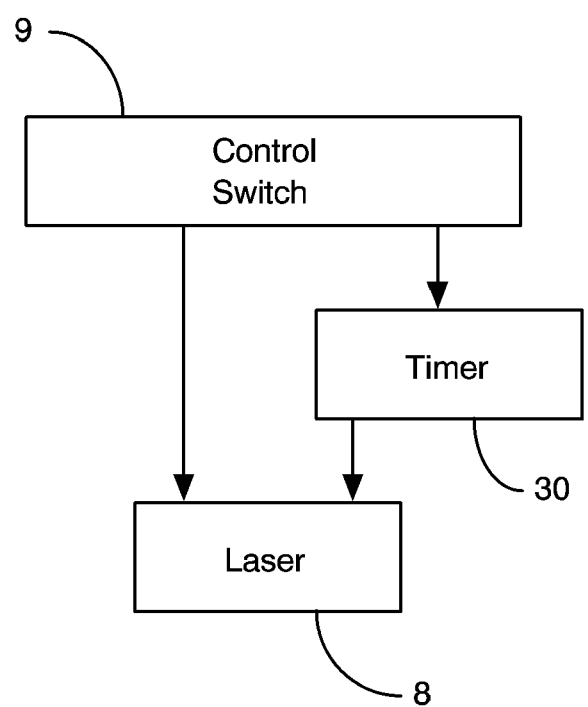
FIG. 12 is a diagram illustrating an alternative embodiment which uses a timer to control the length of time light is applied to the user's scalp.

FIG. 12 is a diagram illustrating an alternative embodiment which uses a timer 30 to control the length of time light is applied to the user's scalp. The timer function allows the device to be activated for a predetermined time period. The time period can be fixed at the factory, or set by the user. In the figure, when the control switch 9 is activated, it signals the laser 8 to begin operation. At the same time, a signal from the control switch is supplied to the timer 30. This activates the timer 30 for the predetermined period of time. When the time period has expired, the timer 30 deactivates the laser 8.

Figure 13A:
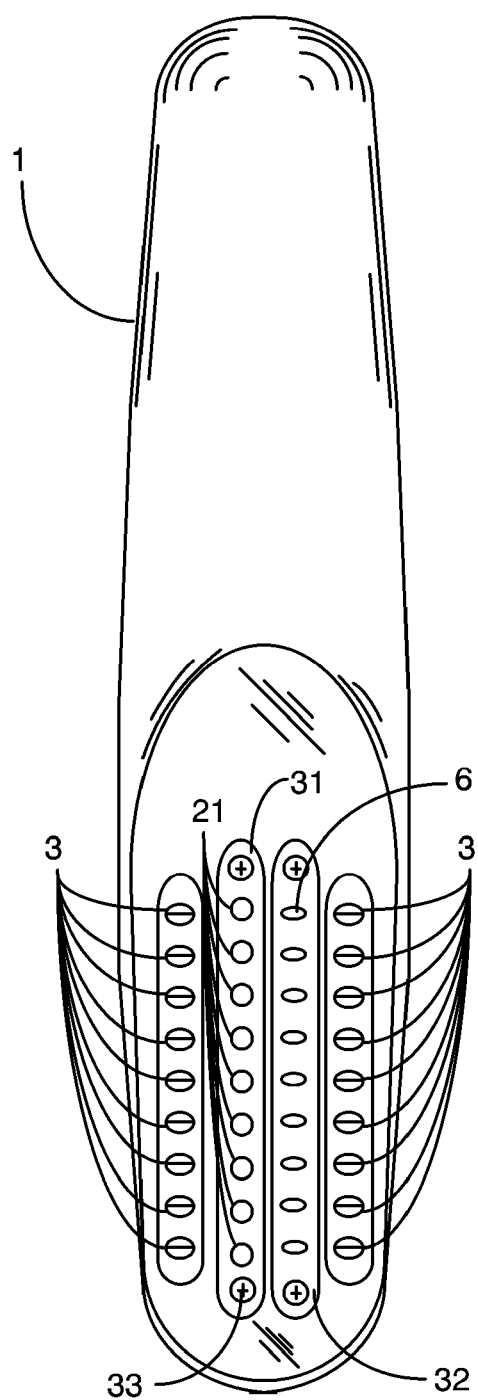
FIG. 13A is a bottom view of an alternative embodiment which uses detachable laser and LED assemblies.

FIG. 13A is a bottom view of an alternative embodiment which uses detachable laser 32 and LED 31 assemblies. The detachable laser 32 and LED 31 assemblies allow a user to replace them if they are damaged of defective. Further, they also allow users to change the detachable laser 32 and LED 31 assemblies for the purpose of changing frequencies or power levels. A significant advantage provided by the detachable laser 32 and LED 31 assemblies is that the alterations can be made at minimum expense and without skilled technical assistance. The figure illustrates screws 33 used to secure the detachable laser 32 and LED 31 assemblies, but those skilled in the art will recognize that any suitable securing method can be used.

Figure 13B:
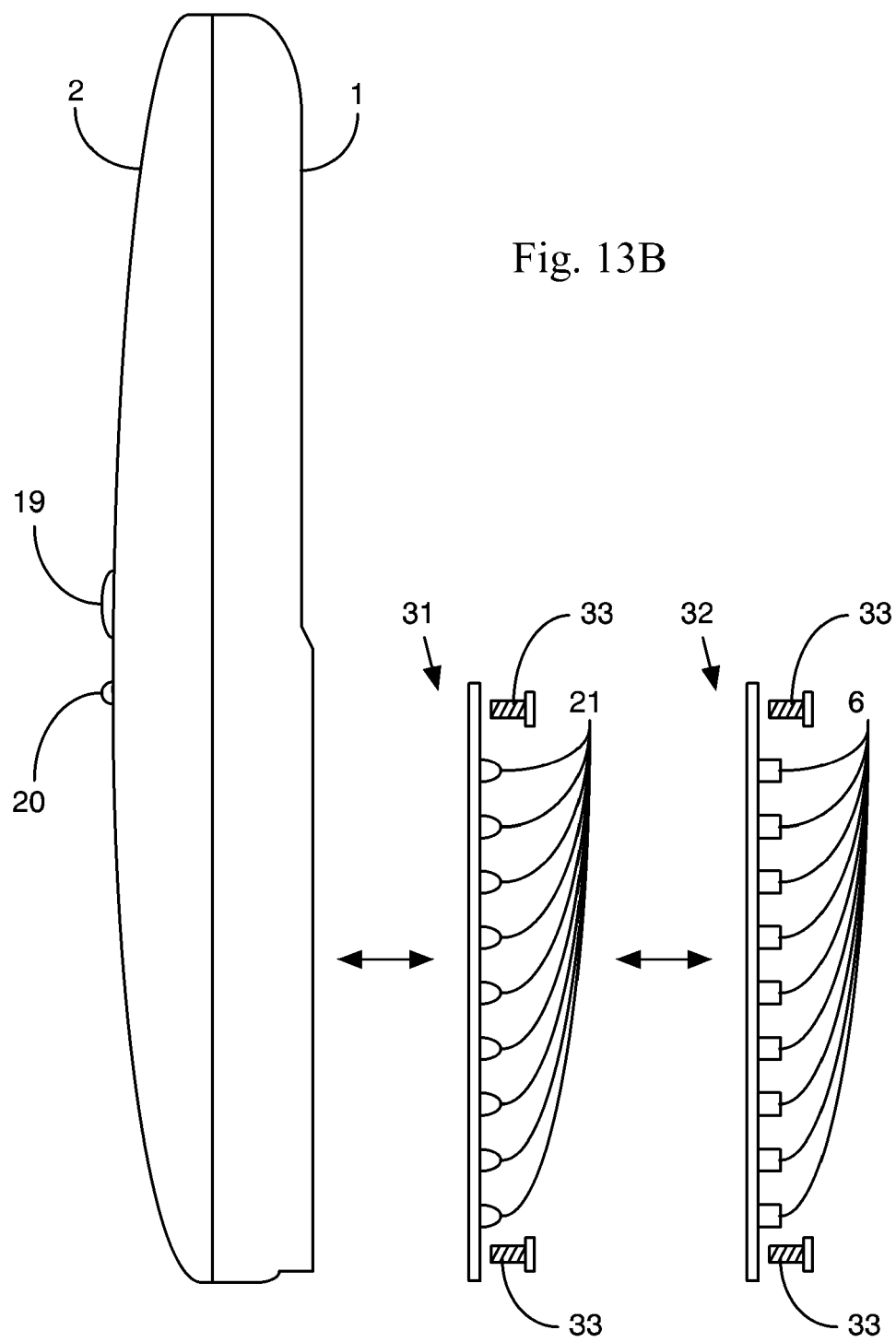
FIG. 13B is a side view of an alternative embodiment which uses detachable laser and LED assemblies.

FIG. 13B is a side view of an alternative embodiment which uses detachable laser 32 and LED 31 assemblies. This figure shows the detachable laser 32 and LED 31 assemblies disconnected from the lower housing 1.

Figure 14:
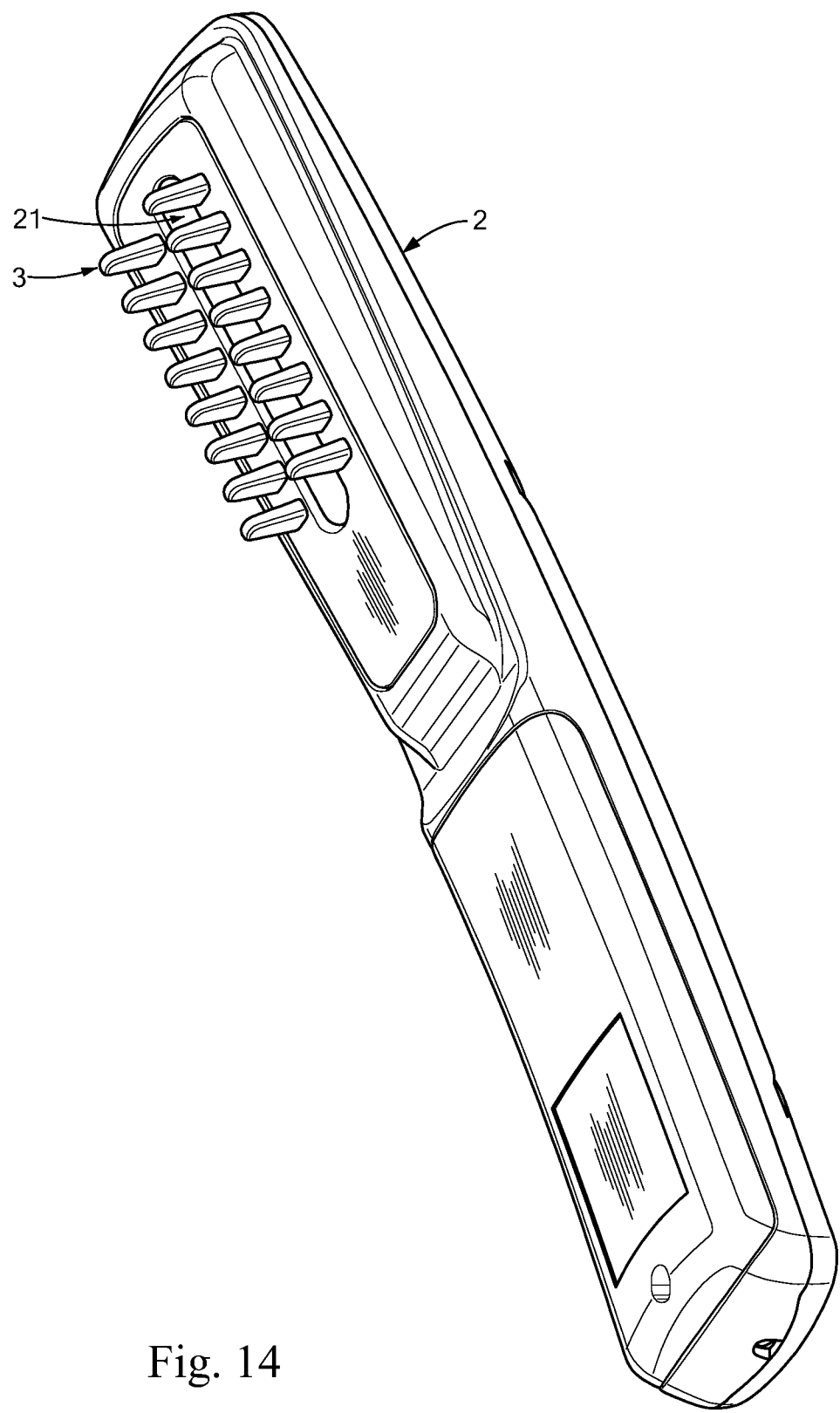
FIG. 14 is perspective view of an alternative embodiment using the LED assembly of FIG. 13B to emit white light.

FIG. 14 illustrates an alternative embodiment of the device where emitters 21 may be any non-coherent light source, whether monochromatic or multichromatic, and may be used on the device without laser 32. For example, multiple emitters 21 may be positioned on the LED 31 assembly as described above. Each emitter 21 may emit, for example, red light, green light, blue light, or a combination thereof to produce white light, or any color light or combination of light in the visible spectrum. For example, an array of white light emitters 21 may be positioned between the teeth 3. Each of the emitters 21 may emit white light, which may be achieved through mixing red, green, blue (RGB) light to produce a white light. Alternatively, three adjacent emitters 21 may cooperate to produce a net white light effect. For example, a first emitter 21 may emit red light, a second green light, and a third blue light. Additionally, white light may be achieved by using, for example, a blue light LED emitter 21 and coating it with a phosphor material to convert the blue light to white light. It is further contemplated that UV or Infrared red light also be emitted from the emitters 21.

Figure 15:
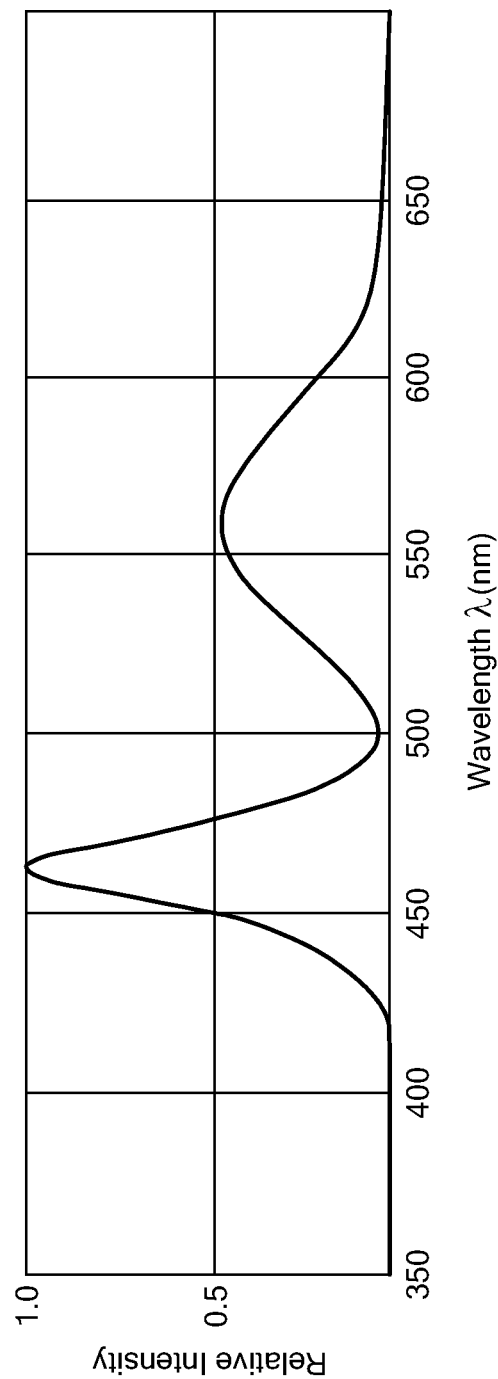
FIG. 15 is a graph of the spectrum of light emitted by an exemplary embodiment of the LED assembly of FIG. 14.

As shown in FIG. 15, the array of emitters 21 produces non-coherent light having at least two intensity peaks. For example, one intensity peak may be between approximately 425 nm and 500 nm, the second between approximately 500 nm and 650 nm, and a third approximately 900 nm to 1200 nm. It is further contemplated that application of white light at these particular wavelengths, or any wavelength, to the scalp may have antimicrobial and healing properties for the scalp, which may facilitate the growth or re-growth of hair. For example, a wavelength of approximately 1180 nm may facilitate hair growth by increasing vascular endothelial growth factors.

The emission of the light from LED 31 assemblies may further be constant or programmed to emit light for a predetermined time duration, or may be pulsed depending on the desired use of the device. Optionally, before, during, or after the emission of light from LED 31 assemblies, the teeth 3 may vibrate, oscillate, rotate or others mechanically move the hair around the teeth 3, to not only part the hair, but to massage the scalp, which may aid in hair growth. For example, a tooth 3 may be pivot longitudinally towards and back from its complementary tooth 3 on the opposite side of the LED 31 assembly. In doing so, the scalp is not only massaged, but the hair is parted for application of light.

Figure 16:
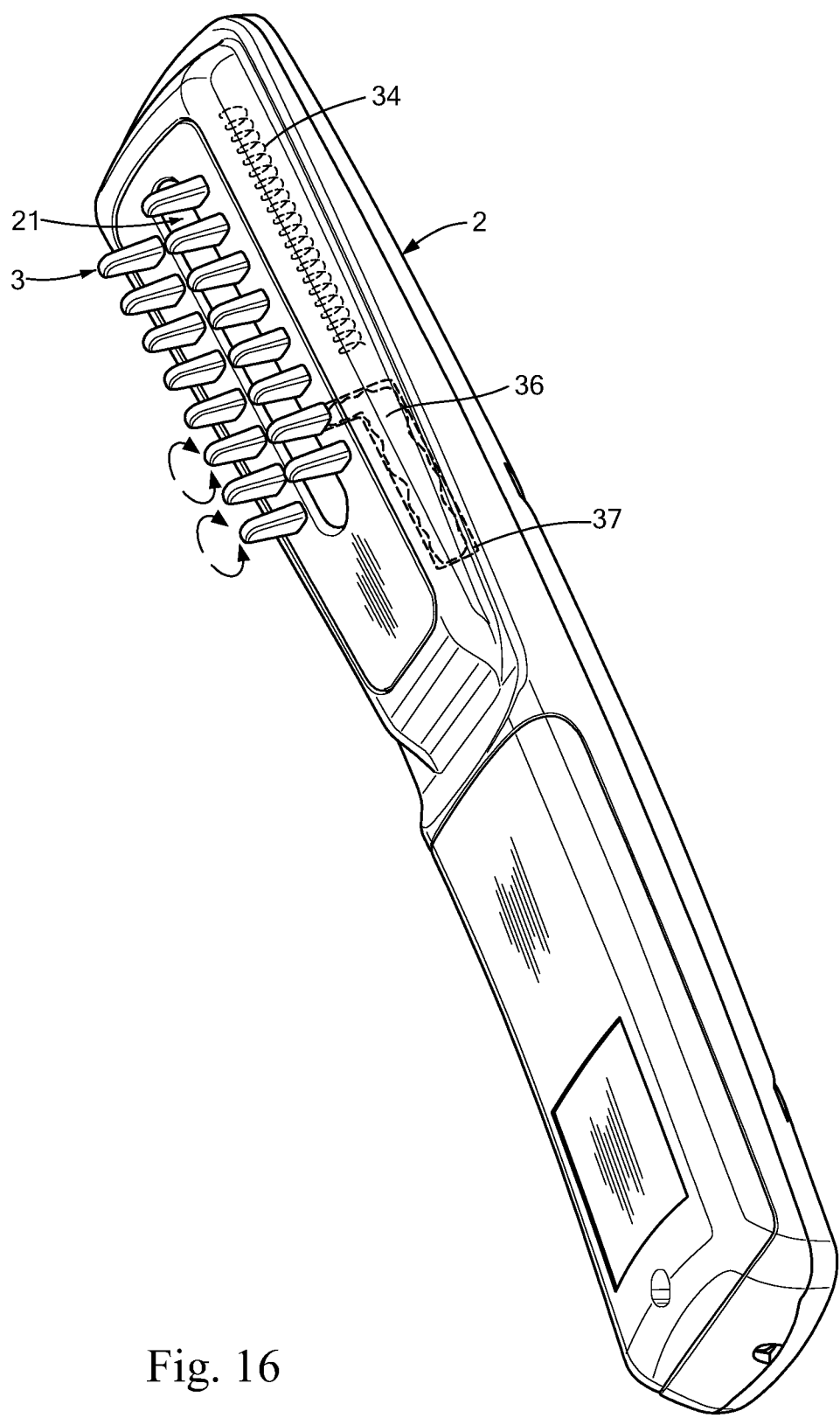
FIG. 16 is a perspective view of an alternative embodiment showing the heating assembly, the vibrating teeth, and the reservoir.

Additionally, the device may include a heating element 34 (FIG. 16) disposed within or about the teeth 3. The heating element 34 may be operable to transmit heat to the scalp before, during, or after emission of light from the emitters 21 from the teeth 3 or from an area proximate the teeth 3 on the device. The heating element 34 may be, for example, a poorly conductive wire coil heated by electricity or an incandescent light disposed on the surface of the housing 2. Proximate the heating element 34 may be a fan that operates to blow air past the heating element 34 and out through an aperture defined by a tooth at its distal end. In exemplary operations of the device, the scalp may be heated by application of heat supplied from the heating element 34 in the form of convective heat (from hot air being blown onto the scalp), conductive heat (from heated teeth 3 applied directly to the scalp), and/or radiation (from one or more of the emitters 21 or the incandescent light source). Heat may be applied before, during, or after oscillation of the teeth 3 as discussed above.

A hair growth stimulation cream 36 may also be included within the device or used complementary to the device by the user. For example, the cream 36 may be disposed within a reservoir 37 defined by the upper housing 2 in fluid communication with the teeth 3. The cream 36 may be a bioactive compound, reacting with the scalp on contact, or a photoactive compound, reacting when light emitted from emitters 21 contacts the cream 36. The cream 36 may be released from the reservoir 37 by activation of a piston or other application element disposed within the reservoir 37 which forces the cream 36 out of the reservoir 37. In an exemplary embodiment, the cream 36 may be forced out of the reservoir 37 through the teeth 3, which may be hollow and define an aperture at its distal end. The cream 36 may be applied to the scalp before, during, or after application of light from emitters 21.

Figure 17:
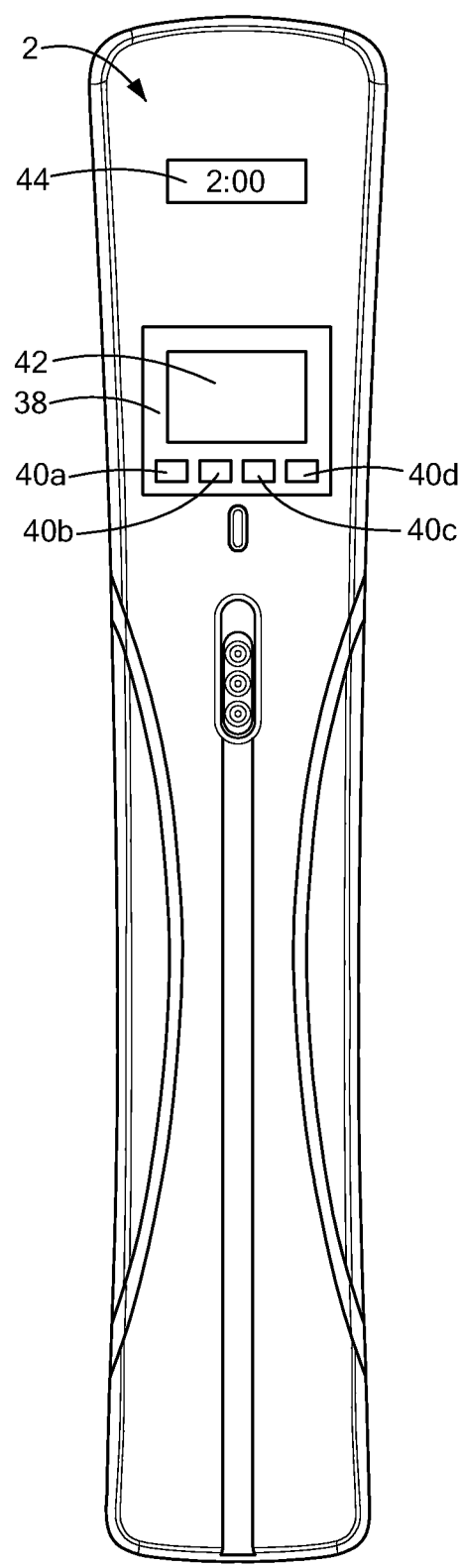
FIG. 17 is a perspective of an embodiment of control element and the controls of the device.

Additionally, each and every feature of the device may be programmable by operation of a control element 38 (FIG. 17) positioned on the device, for example, on the upper housing 2. The control element 38 may include one or more controls 40 that are operable to program the device and a display 42 that displays the programmed information. For example, the controls 40 may include a vibration control 40a, an emitter control 40b, which selects constant, pulsed, or variable light emission, a heating element control 40c, and a cream dispersion control 40d. Each control 40 may be independently selectable and the features activated by selecting each control 40 may be operable simultaneously. For example, both control 40a and 40d may be selected at the same time to operate their respective features simultaneously. Should control 40d be selected, control 40c may be operated on a delay, such that cream 36 can be dispersed without interference from the heating element 36 or causing interference with the application of heat. Additionally, a timer 44 may be included as part of the control element 38. The timer 44 may be programmed such that the selected controls 40a-d may activate their respective features for a pre-set period of time. For example, the timer 44 may be programmed such that each feature controlled by respective controls 40a-d, operates for an effective treatment duration, for example, 2 minutes, and then automatically turns off. This may help to ensure that the user of the device operates it for the desired amount of time.

While the invention has been described with respect to exemplary embodiments thereof, it will be understood by those skilled in the art that various changes in detail may be made therein without departing from the spirit, scope, and teaching of the invention. For example, the material used to construct the device may be anything suitable, the size and shape of the device can vary, the type of laser can vary, etc. Accordingly, the invention herein disclosed is to be limited only as specified in the following claims.

What is claimed is:

1. A device for stimulating hair growth applied to a user's scalp, comprising:
   a housing defining a major axis;
   a plurality of light emitting diodes coupled to the housing operable to emit non-coherent light, the non-coherent light having at least two intensity peaks, wherein the plurality of light emitting diodes emits red, green, and blue light;
   a plurality of pairs of teeth extending from the housing, wherein the plurality of light emitting diodes are disposed between each pair of teeth, each of the plurality of pairs of teeth parts the user's hair to expose the scalp, each of the plurality of light emitting diodes and at least two of the plurality teeth define a longitudinal axis substantially orthogonal to the major axis.

2. The device of claim 1, wherein at least one of the intensity peaks has a wavelength in the range of approximately 425 nm to 500 nm and another of the intensity peaks has a wavelength in the range of 900-1200 nm.

3. The device of claim 1, wherein the plurality of light emitting diodes emits monochromatic light and includes a phosphor material disposed on its surface, wherein the phosphor material converts the monochromatic light to white light.

4. The device of claim 1, further comprising a heating element coupled to the housing and operable to transmit heat to the scalp.

5. The device of claim 4, further comprising a fan disposed within the housing operable to blow heat transmitted from the heating element onto the scalp.

6. The device of claim 1, wherein the plurality of pairs of teeth are movable.

7. The device of claim 1, wherein the housing defines a reservoir, and wherein a photoactive cream is stored within the reservoir.

8. The device of claim 7, wherein the device is operable to deposit the photoactive cream on the user's scalp.

9. The device of claim 1, wherein the plurality of pairs of teeth vibrate.

10. The device of claim 1, further comprising a control element coupled to the housing.

11. A method of stimulating hair growth on a user's scalp, comprising:
- exposing the scalp using a hand-held device, the hand-held device has a plurality of pairs of vibrating teeth operable to part hair;
- emitting non-coherent light having at least two intensity peaks onto the scalp;
- applying a photoactive cream to the scalp; and
- heating the scalp using the hand-held device.

12. The method of claim 11, wherein the non-coherent light is blue light.

13. The method of claim 11, wherein the non-coherent light is emitted in the ranges of approximately 425 nm to 500 nm and approximately 500 nm to 600 nm.

14. The method of claim 11, wherein the hand-held device blows air to expose the scalp.

15. The method of claim 11, wherein the non-coherent light is emitted from a plurality of light emitting diodes.

16. A device for stimulating hair growth applied to a user's scalp, comprising:
- a housing;
- a plurality of white light emitting diodes coupled the housing emitting white light including at least one intensity peak having a wavelength between approximately 900 nm and 1200 nm;
- a plurality of pairs of teeth extending from the housing, wherein the plurality of white light emitting diodes are disposed between each pair of teeth, each of the plurality of pairs of teeth parts the user's hair to expose the scalp; and
- a photoactive cream disposed within the housing, the photoactive cream being dispersible to the scalp.

* * * * *